United States Patent
West

(10) Patent No.: US 6,686,485 B2
(45) Date of Patent: Feb. 3, 2004

(54) SYNTHESIS OF COENZYME Q10, UBIQUINONE

(76) Inventor: Daniel David West, 1 Warren Ct., Rockport, ME (US) 01966

(*) Notice: Subject to any disclaimer, the term of this patent is extended or adjusted under 35 U.S.C. 154(b) by 81 days.

(21) Appl. No.: 09/837,320

(22) Filed: Apr. 19, 2001

(65) Prior Publication Data

US 2002/0156302 A1 Oct. 24, 2002

(51) Int. Cl.[7] ............................................... C07C 50/28
(52) U.S. Cl. ...................................................... 552/307
(58) Field of Search .......................................... 552/307

(56) References Cited

PUBLICATIONS

Eto et al, A novel solvent effect in the practical synthesis of ubiquinone–10, 1988,, vol. 10, pp. 1597–1600.*

* cited by examiner

*Primary Examiner*—Alton N. Pryor
(74) *Attorney, Agent, or Firm*—Evelyn M. Sommer

(57) ABSTRACT

Processes for the stereospecific synthesis of coenzyme Q10, ubiquinone, are disclosed; a semi synthetic procedure using solanesol derived from tobacco waste as the starting material. The process of the invention results in high yields of isometrically useful compositions containing the optically pure isomers.

1 Claim, No Drawings

SYNTHESIS OF COENZYME Q10, UBIQUINONE

BACKGROUND OF THE INVENTION

The invention relates to an improved process for the stereospecific synthesis of Coenzyme Q10, ubiquinone. The present invention also relates to the therapeutically useful optically pure isomers of Coenzyme 10 and refers to new pharmaceutical compositions which contain the optically pure isomers of coenzyme Q10 dissolved or suspended in a suitable vehicle which are useful for example in preventing anoxic tissular damage, particularly in the myocardium. Previous procedures for ubiquinone isolation had several drawbacks; many steps were involved, the yields were low, the intermediates were difficult to purify, overall costs were high, and the final products were obtained as mixtures of isomers, cis(Z) and trans(E).

Coenzyme Q gives reference to a series of quinones which are widely distributed in animals, plants and microorganisms. These quinones have been shown to function in biological electron transport systems which are responsible for energy conversion within living cells. In structure, the coenzyme Q group closely resembles the members of the vitamin K group and the tocopherylquinones, which are derived from tocopherols (vitamin E), in that they all possess a quinone ring attached to a long hydrocarbon tail. The quinones of the coenzyme Q series which are found in various biological species differ only slightly in chemical structure and form a group of related, 2-3-dimethoxy-5-methyl-benzoquinones with a polyisoprenoid side chain in the 6-position which varies in length from 30 to 50 carbon atoms. Since each isoprenoid unit in the chain contains five carbon atoms, the number of isoprenoid units in the side chain varies from 6 to 10. The different numbers of the groups have been designated by a subscript following the Q to denote the number of isoprenoid units in the side chain, as in Q10. Difference in properties are due to the difference in length of the side chain. The members of the group known to occur naturally are Q6 through Q10. Coenzyme Q functions as an agent for carrying out oxidation and reduction within cells. Its primary site of function is in the terminal electron transport system where it acts as an electron or hydrogen carrier between the flavoproteins (which catalyze the oxidation of succinate and reduced pyridine nucleotides) and the cytochromes. This process, is carried out in the mitochondria of cells of higher organisms. Certain bacteria and lower organisms do not contain any coenzyme Q. It has been shown that many of these organisms contain vitamin K, instead and that this quinone functions in electron transport in much the same way as coenzyme Q. Similarly, plant chloroplasts do not contain coenzyme Q, but do contain plastoquinones, which are structurally related to coenzyme Q. Plastoquinone functions in the electron transport process involved in photosynthesis. In some organisms, coenzyme Q is present together with other quinones, such as vitamin K, tocopherylquinones, and plastoquinones; and each type of quinone can carry out different parts of the electron transport functions.

Coenzyme Q10, is a ubiquinone. Ubiquinones are a class of lipid soluble benzoquinones that are involved in mitochondrial electron transport and are essential electron and proton carriers that function in the production of biochemical energy in all cells of aerobic organisms; participating in the transport of electrons from organic substrates to oxygen in the respiratory chain of mitochondria. In addition, coenzyme Q10 has antioxidant and membrane stabilizing properties that serve to prevent cellular damage resulting from normal metabolic processes. It plays an important role as an antioxidant to neutralize potentially damaging free radicals created in part by the energy-generating process. As an energy carrier, coenzyme Q10 is continually going through an oxidation reduction cycle. As each coenzyme Q10 molecule accepts electrons, it is reduced, when it gives up electrons, it becomes oxidized again. In coenzyme Q10's reduced form (ubiquinol), the coenzyme Q 10 molecule holds electrons loosely and will quite easily give up one or two electrons to neutralize free radicals. In its electron rich reduced form, coenzyme Q10 is as potent an antioxidant as vitamin E. Coenzyme Q10's main role as an antioxidant is in the mitochondria where it first participates in the process by which free radicals are generated and then helps to quench the extra free radicals that threaten cellular components such as DNA, RNA, and cell membranes. One of coenzyme Q10's key antioxidant actions is within the cell membrane, where it counters the oxidative attack of polyunsaturated lipids (lipid peroxidation), which causes damage in a self-propagating, destructive chain reaction that ultimately results in membrane degeneration leading to cell death.

In mammalian tissue the quinone ring of coenzyme Q10 is synthesized from the amino acids, tyrosine and phenylalanine and the polyprenyl side chain is synthesized from acetyl-CoA. The number of isoprene units depends on the species, the most common form in mammals contains ten isoprene units. Coenzyme Q10 participates in the transport of electrons from organic substrates to oxygen in the respiratory chain of the mitochondria. During this process ubiquinone is reduced to a free radical semiquinone by the uptake of a single electron. Reduction of this enzyme-bound intermediate by a second electron yields ubiquinol. This a reversible reducible process.

Ubiquinone has a characteristic light absorption band at 270 to 290 nm, which disappears when it is reduced to its quinol form; this spectral change is used to measure oxidation and reduction of ubiquinone.

The structure of coenzyme Q10 consists of a quinone ring attached to an isoprene side chain. It contains 82.08% carbon, 10.51% hydrogen and 7.41% oxygen. Its has a molecular weight of 863.37 and a formula of $C_{59}H_{90}O_4$. The oxidized, intermediate and reduced forms of coenzyme Q10 are shown in the following drawings:

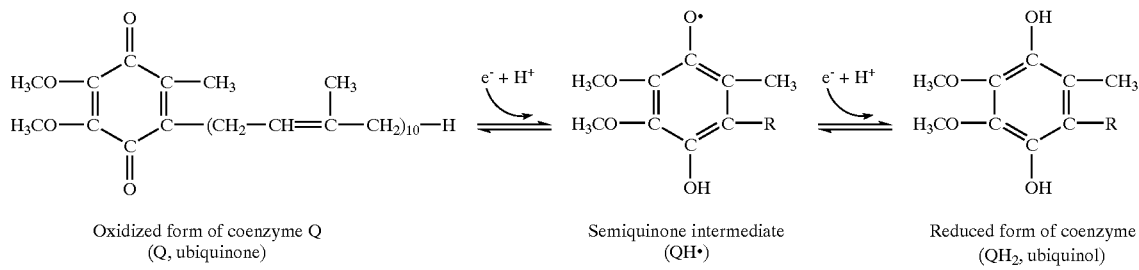

Oxidized form of coenzyme Q
(Q, ubiquinone)

Semiquinone intermediate
(QH•)

Reduced form of coenzyme Q
(QH₂, ubiquinol)

Ubiquinone (Q) is reduced to ubiquinol (QH₂) through a semiquinone intermediate (QH•).

Coenzyme Q10 is used extensively as a nutritional supplement as well as a pharmacological active agent. It has wide use and acceptance in the treatment of cardiovascular disease in traditional as well as alternative medicine. It is used successfully in treating ischemic heart disease, chronic heart failure, toxin induced cardiomyopathy, hypertension and hyperlipidemia. Endogenous coenzyme Q10 functions as an essential cofactor in many metabolic pathways. Its action as an additional pharmacological agent in treatment of such cardiovascular disease processes may be to improve function of the involved tissues that are ischemic or pathologicaily altered by providing an increased energy source, by acting as a free radical scavenger and/or membrane stabilizer. In addition, coenzyme Q10 is found in high concentrations in healthy hearts and at low levels in people with congestive failure leading to the suggestion that supplementation with the coenzyme would be of help in the treatment of heart disease. It is theorized that Coenzyme Q10 might work in the heart in two ways; as an antioxidant to help thwart damage from free radicals that contribute to arterial blockage, and to help boost heart muscle action by improving energy efficiency. Additionally coenzyme Q10 may boost the effects of vitamin E, also a potent antioxidant with some potential beneficial heart effects.

Coenzyme Q10 has been used in the treatment of slow muscle degeneration (dystrophy or atrophy) and the accompanying cardiac complications typically found in these patients In addition to its helper role in the release of energy, Coenzyme Q10 serves as an antioxidant, neutralizing free radicals that cause potentially irreversible damage to cells, tissues, and organs. Coenzyme Q10 is also believed to strengthen the immune system, so as to provide antibacterial and antiviral activity (including HIV), to increase antibody production and to induce the immune system to produce a greater number of immune acting cells. Among the increasing number of pharmacological uses ascribed to coenzyme Q10 are anticancer (in particular breast cancer) activity, in the treatment of periodontal disease, diabetes, Parkinson's, Alzheimer's, Huntington's disease and to help counteract the aging process.

The rationale for its effectiveness in relieving certain brain disorders is that coenzyme Q10 temporarily restores mitochondrial activity in cells. There is evidence that Parkinson's disease, Huntington's disease and some other neurological diseases may impair the mitochondria throughout the body, but particularly in nerve and brain cells. In that case coenzyme Q10 might slow the progression of these diseases. As a potent. antioxidant, coenzyme Q10 might also help prevent the cell death that occurs in these diseases by blocking the buildup of toxic substances. It has also been shown, that coenzyme Q10 lowers levels of lactate in the brains of people with Huntington's disease. Increased lactate suggests a problem with energy metabolism in brain cells.

Free radical damage is thought to be an important contributor to the body wide deterioration that accompanies aging. Laboratory evidence suggests that supplementation with Coenzyme Q10 can at least partially protect against such damage.

It is clear from the literature that activity of coenzyme Q10 is strictly connected with the tissular respiratory processes.

A wide bibliography points out its ability to solve or prevent anoxic tissular damages, particularly in the myocardium.

Other positive effects have been obtained by means of coenzyme Q10 in the treatment of arterial hypertension, of muscular dystrophy, of periodontopathies, of penfigus and of lichen planus.

In all such pathological conditions, it was also noticed that the administration of coenzyme Q10 led to a normalization of tissular concentrations of this enzyme, otherwise scarce.

Coenzyme Q10 is not toxic (there are no reported side effects), no known medical conditions preclude it use. It is generally employed as a supplement, rather than a replacement for standard medical treatment. No known drug interactions have been reported. Daily oral doses vary from 5–10 mg/dosage (15 to 30 mg pro die) to 50–100 mg/dosage (100–200 mg pro die) The administration of even higher dosages up to 400 mg pro die give satisfactory clinical results but it increases sometimes, the pro die effects of the drug. The larger amount usually being given as multiple doses.

There seems to be no limiting factor as to how long the coenzyme Q10 may be taken; individuals have used it continuously for years.

DESCRIPTION OF THE INVENTION

The invention relates to a process for the stereospecific synthesis of coenzyme Q10, ubiquinone. In accordance with one embodiment of the invention, the synthetic process utilizes solanesol sourced from tobacco waste as the starting material. In accordance with another embodiment of the invention the synthetic process utilizes potato leaves as the starting material.

When solanesol derived from tobacco and potato leaves is used as the starting material, the method of production of coenzyme Q 10 involves a semi synthesis, if geraniol is used as the starting material what is involved is a total synthesis. The two methods of synthesis as hereinafter set forth produce high yields of isomerically pure coenzyme Q10. Rather than using huge quantities of costly tobacco leaves in the solanesol process, it has been found that tobacco dust, a waste product of the tobacco industry also can effectively be used as the starting material.

The previous methods of production of Coenzyme Q 10 had many disadvantages. The procedures were lengthy and involved many steps, the resulting yields were low, the intermediates were difficult to purify, overall costs were high and the final products were obtained as mixtures of isomers, cis(Z) and trans(E).

In addition to alleviating the described disadvantages, the processes of the present invention have been found to be stereospecific (selective) producing exclusively the desired all trans(E) isomers.

The following example will serve to illustrate the invention, it being understood that the same is not to be construed in limitation thereof. The optically pure trans (E) isomer is prepared by carrying out the following reaction steps in the sequence shown.

The optically pure trans (E) isomer Q 10 is prepared by carrying out the following reaction steps in the sequence shown.

EXAMPLE

Step 1: Solanesol.

One kg of tobacco dust is shaken with 4 l of hexane for 1.5 hours. The solid is separated by filtration and extracted with a total of 2.4 l of hexane. The combined extracts are evaporated. To the resulting residue are added 140 ml of 2 N KOH in ethanol and 2 g of pyrogallol. The obtained mixture is heated for 1 hour (reflux) under $N_2$. It is then rapidly cooled, 400 mg of a 9:1 mixture of ethanol and water is added and this mixture extracted with hexane (4×400 ml). The extract is dried with sodium sulfate and chromatographed on a column of 300 g of alumina. After elution with a 9:1 mixture of hexane/ether and evaporation, 5 g of solanesol are obtained.

Step 2: Solanesylacetone.

To a solution of 10 g of solanesol obtained in Step 1 in a mixture of 9.5 ml of anhydrous hexane and 13.5 ml anhydrous ether, at 0–5 degree C., there are added 1.3 ml of pyridine. Thereafter over a period of 35 minutes, 1.8 ml of phosphorous tribromide in 13 ml of hexane are added. The resulting mixture is stirred, at 0–5 degrees C. for 3 hours and then added to ice water, and then stirred for an additional 10 minutes. The organic phase is separated off, and the aqueous layer extracted with ether, washed with 5% sodium bicarbonate water, and then dried with magnesium sulfate. After evaporation, 11 g of solanesol bromide are obtained. 2.5 g of ethyl acetoacetate are added to the solanesol bromide followed by the addition of a solution of 0.4 g of sodium in 18 ml absolute alcohol, over a period of 20 minutes while maintaining a temperature of 10 degrees C. The resulting reaction mass is kept at 20 degrees C. for 12 hours. It is then heated to 80 degrees C., and 2.5 ml of 10% NaOH are added over 1 hour. The mixture is then stirred at 80 degrees C. for 4 hours, poured into ice water and extracted with ether, The ether solution is washed with water and dried with magnesium sulfate and evaporated. The yield is 8 g of solanesylacetone obtained as a solid.

The chemical reactions can be seen in the following formulas:

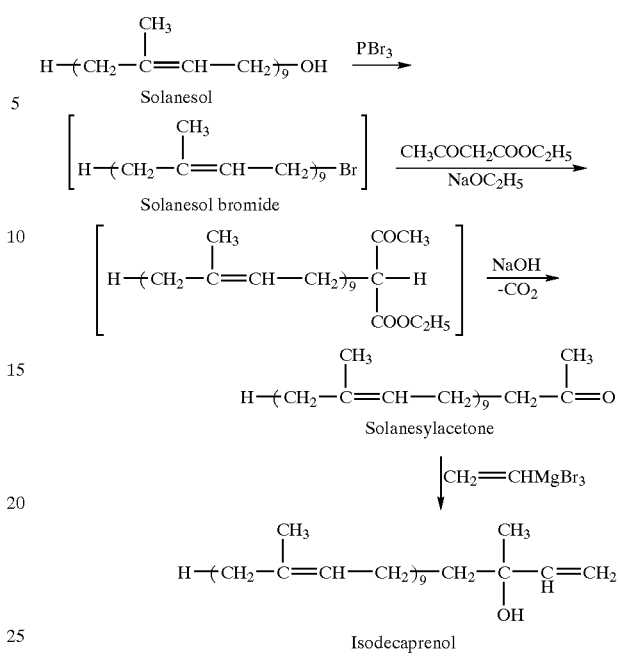

Step 3:—Isodecaprenol.

To 1.4 g of magnesium in 18 ml anhydrous THF (under $N_2$) a small crystal of iodine, a drop of methyl iodide and 0.1 ml of vinyl bromide are added. After the onset of the exothermic reaction, 4 ml vinyl bromide in 9 ml THF are gradually added while the temperature is maintained at about 50 degrees C. The mixture is stirred at 50–60 degrees C. for 1 hour to complete the formation of vinyl-magnesium bromide. The mixture is then cooled to 0–5 degrees C. and 8 g of solanesylacetone in 32 ml THF are added over a period of 10 minutes. The mixture is left at 20 degrees C. for 3 hours after which it is cooled to 0–5 degrees C. A solution of 4.2 g ammonium chloride in 10 ml of water is added, and mixture is stirred for 10 minutes and is then extracted with ether, washed with water and dried with magnesium sulfate. After evaporation, 9 g of isodecaprenol were obtained as a colorless, waxy substance.

Step 4:—2, 3, 6-tribromo-4-methylphenol—9108 g (1 mol) p-cresol is dissolved in 120 l of chloroform containing 4 g iron powder and 500 g bromine are then introduced drop wise over a period of 5 hours at room temperature. The resulting solution is stirred for 48 hours and then filtered, washed with dilute sodium sulfite and dried with magnesium sulfate. The solvent is evaporated and the residue recrystallized from hexane. A yield of 265 g is obtained.

2,3,6-Tribromo-4-methylphenol

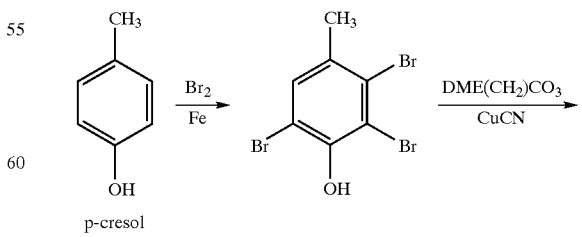

p-cresol

Step 5:—2,3,4,5-tetramethoxytoluene.

Sodium (23 g) is dissolved in 400 ml of methanol. To this 9.3 g DME and 50 ml dimethyl carbonate are added to the resulting solution. Most of the methanol (300 ml) is then removed by distillation; 915 g of copper cyanide are added and a solution of 34.4 g 2,3,6-tribromo4-methylphenol in 100 ml DME prepared and is added drop wise over a period of 3 hours, with stirring, while maintaining the temperature at 80 degrees C. The mixture is stirred an additional 5 hours while continuing to maintain the 80 degrees C. temperature. To this mixture, 800 ml of water is added, the mixture is cooled to 50 degrees C. 100 ml Dimethyl sulfate is then added in drop wise fashion. The mixture is then stirred at room temperature for 2 hours and concentrated. 250 Ml aqueous ammonium hydroxide are then added. The mixture is extracted with methylchloride and the organic extract washed with dilute HCl and water and dried over magnesium sulfate. The solvent is evaporated off leaving 20 g of pure product; bp 100 C. (0.1 mm).

2,3,4,5-Tetramethoxytoluene

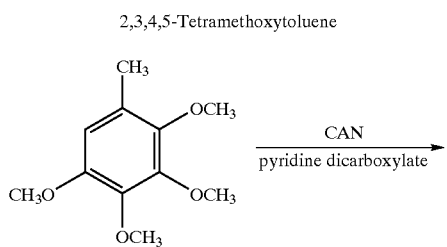

Step 6:—2,3 dimethoxy-5-methylhydroquinone.

33.4 g of Pyridine-2,6 dicarboxylate was added to a cold, 0 degree C., solution of 2,3,4,5 tetramethoxytoluene (17 g) in 400 ml of acetonitrile/water (7:3). A cold solution, 0 degree C., of ceric ammonium nitrate, 110 g in 400 ml of 1:1 acetonitrile/water is slowly added over 20 minutes, and the mixture stirred for 20 minutes at 0 degree C. and for 10 minutes at room temperature. The reaction mixture is poured into 400 ml of water and extracted with methyl chloride. The organic layer is dried over magnesium sulfate, evaporated and chromatographed on silica gel, hexane/ethylacetate 20:1, yielding 14 g of red crystals, mp 59 degrees C.

2,3-Dimethoxy-5-methylhydroquinone

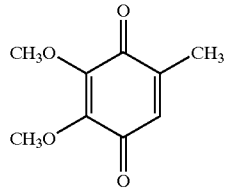

Step 7:—Ubiquinone Coenzyme Q 10.

Equimolar portions of portions of the products obtained in step 3 (isodecaprenol) and 6 (2, 3 dimethoxy-5-methyl hydroquinone) are stirred at 43 degrees C. for 10 minutes in hexane. A 2.5% sodiumbisulfite solution is added, and the hexane layer separated, dried over magnesium sulfate, concentrated and chromatographed on silica gel (hexane/ether 10:1) to give ubiquinone as a yellow solid.

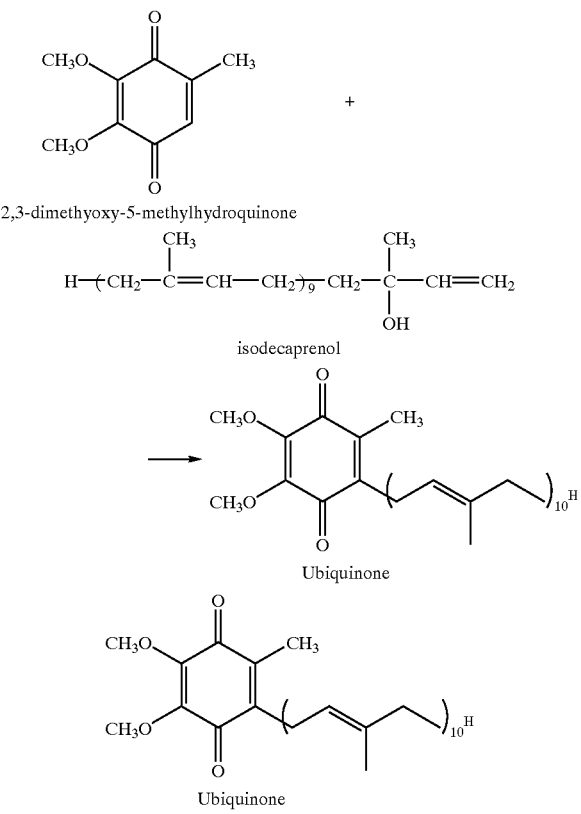

The administration of optically pure Coenzyme Q10 can be oral, parenteral or topically, in the latter case for the treatment of diseases of skin and mucous membranes. Oral administration is favored over parenteral administration due to the very low solubility of coenzyme Q10 in excipients compatible with is parenteral administration. Oral administration has proved particularly useful in the treatment of diseases affecting metabolically very active organs, whereas coenzyme Q 10 if administered orally proves to be substantially ineffective at the cutaneous level. Accordingly the concentration of Coenzyme Q 10 has to be increased for topical administration directly to impaired or damaged tissue.

The oral form of administration can be as pills, tablets, capsules or liquid preparations in each case formulated in the conventional manner with suitable carriers and formulation aids. The formulations are prepared to deliver 5–100 mg per dosage unit and in some instances up to 200 mg per dosage units of the optically pure coenzyme Q 10.

The compositions for topical administration can be prepared by dissolving or suspending coenzyme Q 10 in vegetable oils such as corn oil, canola oil, or soy bean oil, lecithin, glycerol, glycerylfurole, Tween 80 or other derivatives, suspending agents or diluents. After the addition of suitable carriers and formulation aids to such solutions or suspensions, the compositions can be forwarded as pastes, creams, ointments, gels, lotions, unguents.

The compositions for topical application contain the optically pure coenzyme 10 as the active principal in amounts from 0.1 to 10%, preferably from 0.25 to 1%. The topical compositions can also be used for cosmethological purposes. In such a case, the content of coenzyme Q 10 can be lower than the limits aforementioned being preferably from 0.0001 to 0.1%.

The compositions in any application form may also contain other topically active components beside the active principle (optically active coenzyme Q 10).

I claim:
1. A stereospecific synthesis of optically pure trans (E) isomer of coenzyme Q 10 having the formula

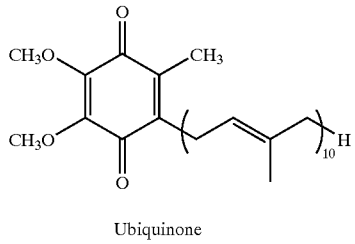

Ubiquinone which comprises extracting solanesol from tobacco dust using hexane and using said solanesol as the starting material for carrying out the following sequence of reactions resulting in the formation of isodecaprenol,

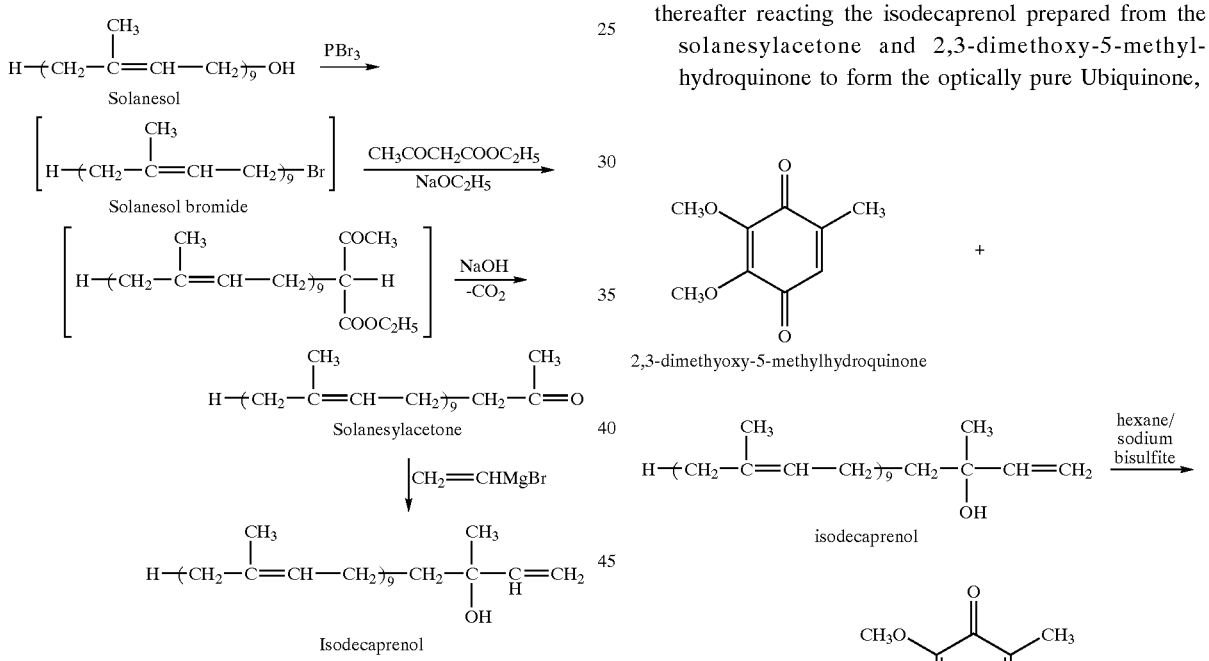

separately carrying out the following:

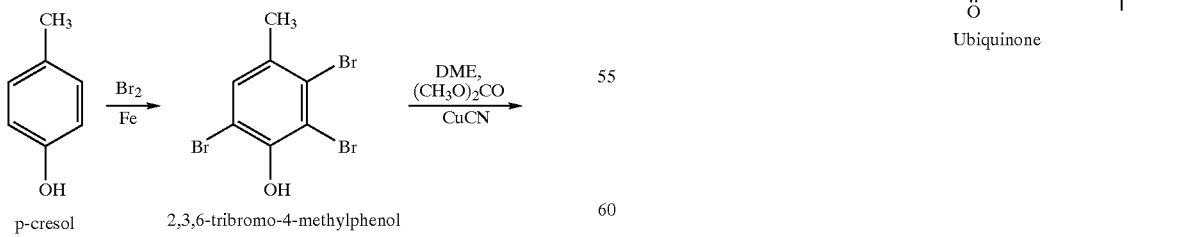

-continued

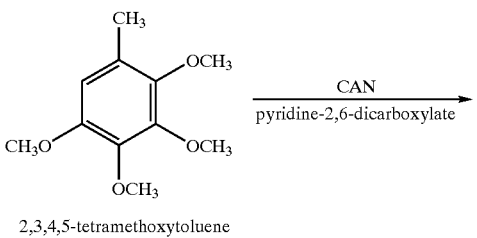

2,3,4,5-tetramethoxytoluene

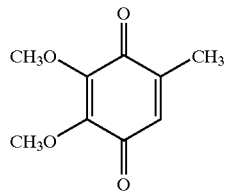

2,3-dimethoxy-5-methylhydroquinone thereafter reacting the isodecaprenol prepared from the solanesylacetone and 2,3-dimethoxy-5-methyl-hydroquinone to form the optically pure Ubiquinone,

* * * * *